(12) United States Patent
Murugesan et al.

(10) Patent No.: US 8,440,823 B2
(45) Date of Patent: May 14, 2013

(54) PROCESS FOR THE PREPARATION OF ERLOTINIB OR ITS PHARMACEUTICALLY ACCEPTABLE SALTS THEREOF

(75) Inventors: Balaguru Murugesan, Coimbatore (IN); Anandam Vempali, Nellore (IN); Swargam Sathyanarayana, Karim Nagar (IN); Rajesh Kumar Thaper, Banjara Hills (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/258,961

(22) PCT Filed: Mar. 26, 2010

(86) PCT No.: PCT/IB2010/051343
§ 371 (c)(1),
(2), (4) Date: Jan. 4, 2012

(87) PCT Pub. No.: WO2010/109443
PCT Pub. Date: Sep. 30, 2010

(65) Prior Publication Data
US 2012/0101272 A1    Apr. 26, 2012

(30) Foreign Application Priority Data

Mar. 26, 2009 (IN) .............................. 596/DEL/2009
Mar. 4, 2010 (IN) .............................. 483/DEL/2010

(51) Int. Cl.
*C07D 401/00* (2006.01)
(52) U.S. Cl.
USPC ........................................................ 544/284
(58) Field of Classification Search ................ 514/266.1; 544/283, 284
See application file for complete search history.

(56) References Cited

U.S. PATENT DOCUMENTS

| 6,476,040 | B1 | 11/2002 | Norris et al. ................ | 514/259 |
| 6,900,221 | B1 | 5/2005 | Norris et al. ................ | 514/266.4 |
| 7,148,231 | B2 | 12/2006 | Bubendorf et al. ......... | 514/266.4 |
| 2005/0130995 | A1 | 6/2005 | Nishino et al. ............. | 514/266.4 |
| 2006/0154941 | A1 | 7/2006 | Huang ........................ | 514/266.4 |
| 2008/0058355 | A1 | 3/2008 | Westheim .................. | 514/236.8 |
| 2008/0167327 | A1 | 7/2008 | Westheim .................. | 514/266.4 |

FOREIGN PATENT DOCUMENTS

| EP | 0 817 775 | 9/2001 |
| EP | 0817775 | * 12/2001 |
| EP | 1 044 969 | 12/2006 |
| WO | WO 99/55683 | 11/1999 |
| WO | WO 01/34574 | 5/2001 |
| WO | WO 03/066602 | 8/2003 |
| WO | WO 2004/072049 | 8/2004 |
| WO | WO 2007/060691 | 5/2007 |
| WO | WO 2007/138612 | 12/2007 |
| WO | WO 2007/138613 | 12/2007 |
| WO | WO 2008/000418 | 1/2008 |
| WO | WO 2008/012105 | 1/2008 |
| WO | WO 2008/049645 | 5/2008 |
| WO | WO 2008/102369 | 8/2008 |
| WO | WO 2008/122776 | 10/2008 |
| WO | WO 2009/002538 | 12/2008 |
| WO | WO 2009/007984 | 1/2009 |
| WO | WO 2009/024989 | 2/2009 |
| WO | WO 2009/025873 | 2/2009 |
| WO | WO 2009/025876 | 2/2009 |

OTHER PUBLICATIONS

Norris and Santafianos, "Discovery of a new stable polymorph of 4-(3-ethynylphenylamino)-6,7-bis(2-methoxyethoxy)quinazolinium methanesulfonate using near-infrared spectroscopy to monitor form change kinetics", *Journal of the Chemical Society, Perkin Transactions* 2,12:2498-2502 (2000).
Hanna et al., "Synthesis and Biological Activity of $N^4$-methyl-5-Azacytidines", *Collection of Czechoslovak Chemical Communications*, 63:713-722 (1998).
Debeljak-Šuštar et al., "Neighboring Group Interaction in Ortho-Substituted Aminopyridines. Pyridopyrimidines and Related Systems", *Journal of Organic Chemistry*, 43(3):393-397 (1978).
Bitha et al., "Cyclocondensation Reactions of 3-Amino-2-hydrazino-4(3H)-pyrimidinones. Formation of 1,2,4-Triazolo[4,3-a]pyrimidines and Pyrimido[1,2-b][1,2,4,5]tetrazines", *Journal of Organic Chemistry*, 52(11):2220-2223 (1987).
Nomoto et al., "Studies of Cardiotonic Agents. 8. Synthesis and Biological Activities of Optically Active 6-(4-(Benzylamino)-7-quinazolinyl)-4,5-dihydro-5-methyl-3(2H)-pyridazinone (KF15232)", *Journal of Medicinal Chemistry*, 39(1):297-303 (1996).

* cited by examiner

*Primary Examiner* — Paul V. Ward (57) ABSTRACT

The present invention relates to a process for preparation of erlotinib of Formula I or its pharmaceutically acceptable salt thereof. The present invention also relates to process for the preparation of erlotinib trifluoroacetate. The present invention also relates to a nove-lCrystalline form of erlotinib trifluoroacetate designated as Form E and process for its preparation. The present invention further relates to process for the preparation of erlotinib hydrochloride from erlotinib trifluoroacetate.

10 Claims, 4 Drawing Sheets

| Pos. [°2Th.] | FWHM [°2Th.] | Area [cts*°2Th.] | d-spacing [Å] | Height [cts] | Rel. Int. [%] |
|---|---|---|---|---|---|
| 3.5656 | 0.0836 | 14.06 | 24.78023 | 170.35 | 1.12 |
| 4.9392 | 0.1004 | 45.14 | 17.89148 | 455.88 | 3.00 |
| 6.0072 | 0.1171 | 661.06 | 14.71279 | 5723.04 | 37.67 |
| 6.4394 | 0.1004 | 1504.36 | 13.72625 | 15194.37 | 100.00 |
| 7.1428 | 0.0836 | 41.25 | 12.37647 | 499.92 | 3.29 |
| 7.3976 | 0.1171 | 200.65 | 11.95939 | 1737.11 | 11.43 |
| 7.9265 | 0.0836 | 202.16 | 11.15413 | 2450.17 | 16.13 |
| 8.0768 | 0.0669 | 97.94 | 10.94685 | 1483.86 | 9.77 |
| 9.6845 | 0.2007 | 17.32 | 9.13292 | 87.47 | 0.58 |
| 10.7767 | 0.2676 | 17.57 | 8.20967 | 66.55 | 0.44 |
| 11.5739 | 0.2007 | 32.31 | 7.64591 | 163.19 | 1.07 |
| 12.0228 | 0.1338 | 37.58 | 7.36146 | 284.65 | 1.87 |
| 12.3853 | 0.0836 | 66.00 | 7.14683 | 799.95 | 5.26 |
| 12.9408 | 0.1338 | 293.30 | 6.84131 | 2221.30 | 14.63 |
| 14.0763 | 0.1004 | 32.68 | 6.29180 | 330.12 | 2.17 |
| 14.5338 | 0.1338 | 83.48 | 6.09479 | 632.39 | 4.16 |
| 15.1686 | 0.1596 | 63.60 | 5.84109 | 428.23 | 2.82 |
| 15.7493 | 0.1171 | 269.80 | 5.62702 | 2335.71 | 15.37 |
| 15.9347 | 0.1004 | 191.99 | 5.56197 | 1939.18 | 12.76 |
| 16.7333 | 0.1171 | 359.89 | 5.29771 | 3115.68 | 20.51 |
| 17.7796 | 0.1338 | 136.02 | 4.98878 | 1030.37 | 6.78 |
| 18.4250 | 0.2007 | 120.85 | 4.81544 | 610.38 | 4.02 |
| 18.9376 | 0.2007 | 132.87 | 4.68624 | 670.99 | 4.42 |
| 19.3950 | 0.0669 | 80.83 | 4.57674 | 1224.64 | 8.06 |
| 20.5301 | 0.2342 | 476.42 | 4.32827 | 2062.25 | 13.57 |
| 20.9077 | 0.1673 | 441.22 | 4.24892 | 2673.86 | 17.60 |
| 21.4334 | 0.1596 | 441.42 | 4.14588 | 2972.27 | 19.56 |
| 22.5564 | 0.1338 | 539.96 | 3.94195 | 4090.25 | 26.92 |
| 23.5436 | 0.2175 | 495.80 | 3.77899 | 2311.24 | 15.21 |
| 24.1309 | 0.3676 | 258.33 | 3.68819 | 981.46 | 6.46 |
| 25.2576 | 0.1673 | 323.30 | 3.52615 | 1959.23 | 12.89 |
| 25.7367 | 0.1596 | 918.24 | 3.46292 | 6129.04 | 40.34 |
| 26.2533 | 0.1338 | 438.85 | 3.39463 | 3445.58 | 22.68 |
| 26.5099 | 0.2676 | 699.01 | 3.36236 | 2647.57 | 17.42 |
| 26.7596 | 0.1338 | 349.21 | 3.33154 | 2645.28 | 17.41 |
| 27.2173 | 0.1673 | 233.98 | 3.27658 | 1436.10 | 9.45 |
| 29.2813 | 0.1673 | 98.48 | 3.05011 | 596.79 | 3.93 |
| 30.7862 | 0.1338 | 83.83 | 2.90438 | 635.02 | 4.18 |
| 31.7833 | 0.2676 | 62.16 | 2.81550 | 235.43 | 1.55 |
| 33.9565 | 0.4015 | 48.25 | 2.64012 | 101.64 | 0.67 |
| 34.8477 | 0.2676 | 40.21 | 2.57461 | 152.28 | 1.00 |
| 38.2352 | 0.4015 | 43.05 | 2.35454 | 108.71 | 0.72 |

PROCESS FOR THE PREPARATION OF ERLOTINIB OR ITS PHARMACEUTICALLY ACCEPTABLE SALTS THEREOF

FIELD OF THE INVENTION

The present invention relates to a process for the preparation of erlotinib of Formula I or its pharmaceutically acceptable salt thereof. The present invention relates to the process for the preparation of erlotinib trifluoroacetate. The present invention also relates to a novel crystalline form of erlotinib trifluoroacetate designated as Form E and process for its preparation. The present invention further relates to process for the preparation of erlotinib hydrochloride from erlotinib trifluoroacetate.

BACKGROUND OF THE INVENTION

Erlotinib of Formula I, chemically N-(3-ethynylphenyl)-6,7-bis(2-methoxyethoxy)-4-quinazolinamine, is indicated for the treatment of patients with locally advanced or metastatic non-small cell lung cancer after failure of at least one prior chemotherapy regimen, and in combination with gemcitabine is indicated for the first-line treatment of patients with locally advanced, unresectable or metastatic pancreatic cancer.

Formula I

Erlotinib is administered as its hydrochloride salt and is currently marketed as TARCEVA® (erlotinib) tablets. Erlotinib hydrochloride has the molecular formula $C_{22}H_{23}N_3O_4 \cdot HCl$ and a molecular weight of 429.90. It is very slightly soluble in water, slightly soluble in methanol and practically insoluble in acetonitrile, acetone, ethyl acetate and hexane.

European Patent No. EP 0 817 775 (herein after "the '775 patent") provides a process for the preparation of erlotinib, which involves adding 3-ethynylaniline and 4-chloro-6,7-bis(2-methoxyethoxy) quinazoline in isopropanol containing pyridine, and then refluxing the mixture for 4 hours under the atmosphere of dry nitrogen. The solvent is removed and residue is extracted in 10% methanol in chloroform and saturated aqueous sodium bicarbonate. N-(3-ethynylphenyl)-6,7-bis(2-methoxyethoxy)-4-quinazolinamine base is separated chromatographically and converted to the hydrochloride salt in a solvent, such as, chloroform using hydrochloric acid. Though the '775 patent mentions few erlotinib acid-addition salt, for example, erlotinib salt with an inorganic or organic acid, such as, hydrochloric, hydrobromic, sulphuric, phosphoric, methanesulfonic, benzenesulfonic, trifluoroacetic, citric, lactic or maleic acid, it only exemplifies the process for the preparation of erlotinib hydrochloride.

European Patent No. EP 1 044 969 provides a process for preparing N-(3-ethynylphenyl)-6,7-bis(2-methoxyethoxy) quinazolin-4-amine which involves stirring 4-[3-[[6,7-bis(2-methoxyethoxy)-4-quinazolinyl]amino]phenyl]-2-methyl-3-butyn-2-ol with anhydrous sodium hydroxide and 2-methoxyethanol and heating at reflux for 47 hours. The reaction mixture is cooled to 20° C. to 25° C. and concentrated hydrochloric acid is added to it. The resulting mixture is granulated at 20° C. to 25° C. to crystallize the product.

PCT Publication No. WO 2008/122776 A2 (herein after "the WO '776 application") provides a process for the preparation of erlotinib salts, such as, erlotinib hydrochloride, erlotinib sulphate, erlotinib tosylate and erlotinib oxalate by reacting 4-halo-6,7-bis(2-methoxyethoxy)quinazoline with 3-aminophenyl acetylene or an acid salt thereof under acidic conditions to give corresponding acid salt of erlotinib.

PCT Publication WO 2007/138612 provides a process for preparation of N-(3-ethynylphenyl)-6,7-bis(2-methoxyethoxy)-4-quinazolinamine hydrochloride which involves reacting 3,4-dihydroxy benzaldehyde with substituted ethylmethyl ether in the presence of an inert solvent and base to obtain 3,4-bis(2-methoxyethoxy)benzaldehyde. The 3,4-bis(2-methoxyethoxy)benzaldehyde is converted to 3,4-bis(2-methoxyethoxy)benzaldoxime in the presence of a base and organic solvent and is further dehydrated to 3,4-bis(2-methoxyethoxy)benzonitrile. The benzonitrile so obtained is nitrated to obtain 4,5-bis(2-methoxyethoxy)-2-nitrobenzonitrile which is further reduced to obtain 2-amino-4,5-bis(2-methoxyethoxy)benzonitrile. N'-(3-ethynylphenyl)-N,N-dimethyl formamidine obtained by formylation of 3-ethynylaniline with N,N-dimethyl formamidine is coupled with 2-amino-4,5-bis(2-methoxyethoxy)benzonitrile to obtain erlotinib free base which upon treatment with a polar solvent containing hydrochloric acid gives erlotinib hydrochloride.

PCT Publication WO 2007/138613 provides a process for preparation of N-(3-ethynylphenyl)-6,7-bis(2-methoxyethoxy)-4-quinazolinamine hydrochloride which involves reacting 3,4-dihydroxy benzaldehyde with substituted ethylmethyl ether in the presence of an inert solvent and base to obtain 3,4-bis(2-methoxyethoxy)benzaldehyde. The 3,4-bis(2-methoxyethoxy)benzaldehyde is converted to 3,4-bis(2-methoxyethoxy)benzaldoxime in the presence of a base and organic solvent and is further dehydrated to 3,4-bis(2-methoxyethoxy)benzonitrile. The benzonitrile so obtained is nitrated to obtain 4,5-bis(2-methoxyethoxy)-2-nitrobenzonitrile which is further reduced to get 2-amino-4,5-bis(2-methoxyethoxy)benzonitrile. 2-amino-4,5-bis(2-methoxyethoxy) benzonitrile is formylated with N,N-dimethyl formamidine to obtain N'-[2-cyano-4,5-bis(2-methoxyethoxy)phenyl]-N,N-dimethylformamidine which is coupled with an 3-ethynylaniline to obtain erlotinib free base which on treatment with a polar solvent containing hydrochloric acid gives erlotinib hydrochloride.

J. Chem. Soc., Perkin Trans. 2, 2000, 2498-2502 provides process for the preparation of erlotinib mesylate by treating erlotinib hydrochloride in water-ethylacetate with 50% aqueous sodium hydroxide solution at 50° C. and separating organic layer, filtering through short pad of celite, the resulting solution is warmed to 50° C. to redissolve precipitated free base, followed by treating the solution with methane sulphonic acid to give a white precipitate, which upon cooling for 4 hours gives erlotinib methane sulphonate.

Several processes have been reported for the preparation of erlotinib or pharmaceutically acceptable salts and their polymorphs, for example, in U.S. Pat. Nos. 6,476,040 B1; 6,900,221 B1; 7,148,231 B2; U.S. Publication Nos. 2005/0130995; 2006/0154941; 2008/0167327 A1; 2008/0058355 A1; PCT Publication Nos. WO 99/55683; WO 2001/034574; WO 2003/066602 A1; WO 2004/072049; WO 2007/060691; WO 2008/000418 A2; WO 2008/012105; WO 2008/049645; WO 2008/102369; WO 2008/122776; WO 2009/002538; WO 2009/007984; WO 2009/024989; WO 2009/025873 A2; WO 2009/025876 A2.

Since erlotinib constitutes an important therapeutic agent, additional and improved ways of preparing erlotinib and its salts are of value to pharmaceutical science. Thus, there is a need in the development of a consistent and novel process for preparing erlotinib and its salts which is commercially viable, safer for handling, less time consuming and of greater purity.

The present inventors have found a process for the preparation of erlotinib or its pharmaceutically acceptable salt thereof, which involves preparing erlotinib or its pharmaceutically acceptable salt thereof directly from 2-amino-4,5-bis (2-methoxyethoxy)benzonitrile and avoiding the usage of corrosive chemicals, such as, phosphorus oxychloride/thionyl chloride. The present inventors also found a process for the preparation of erlotinib trifluoroacetate.

The present inventors have also found that erlotinib hydrochloride can be easily prepared in high purity directly from erlotinib trifluoroacetate without the formation of erlotinib base. The present inventors have also prepared erlotinib trifluoroacetate in a novel polymorphic form, designated as Form E. The novel polymorphic Form E of erlotinib trifluoroacetate of the present invention is suitable for preparing pharmaceutical compositions comprising erlotinib trifluoroacetate.

SUMMARY OF THE INVENTION

In one general aspect there is provided a process for preparing erlotinib of Formula I or its pharmaceutically acceptable salts thereof.

Formula I

The process includes treating 2-amino-4,5-bis(2-methoxyethoxy)benzonitrile of Formula I, Formula II with 3-ethynyl aniline of Formula III Formula III and a compound of Formula IV $$HC(OR)_3 \quad \text{Formula IV}$$

wherein R is alkyl group.

Embodiments of the present aspect may include one or more of the following features. For example, the process may further include the addition of an acid catalyst selected from the group comprising of acetic acid, trifluoroacetic acid, formic acid. The process may also include heating the mixture obtained to reflux at a temperature in the range of 30° C. to 135° C.

The alkyl group of compound of Formula IV may include 1 to 6 carbon atoms. For example, the compound of Formula IV may be triethyl orthoformate. In addition, the pharmaceutically acceptable salts of erlotinib may be prepared by treating erlotinib with an acid in a suitable solvent.

In another general aspect there is provided a process for the preparation of erlotinib trifluoroacetate. The process includes:
a) treating erlotinib base with trifluoroacetic acid; and
b) isolating erlotinib trifluoroacetate.

Embodiments of this aspect may include one or more of the following features. For example, the erlotinib base may be dissolved or slurried in an organic solvent or obtaining an existing solution from a previous processing step of erlotinib base in an organic solvent.

The treatment of erlotinib base with trifluoroacetic acid may be carried at a temperature of about 20° C. to about reflux. Isolation of the erlotinib trifluoroacetate may be carried out by filtration, solvent removal, layer separation, centrifugation, concentration, distillation, or a combination thereof.

In another general aspect there is provided a process for the preparation of erlotinib trifluoroacetate. The process includes:
a) mixing of 2-amino-4,5-bis(2-methoxyethoxy)benzonitrile, 3-ethynyl aniline and Compound of Formula IV, wherein R is alkyl group;

$$HC(OR)_3 \quad \text{Formula IV}$$

b) contacting the mixture obtained in step a) with trifluoroacetic acid; and
c) isolating erlotinib trifluoroacetate.

Embodiments of this aspect may include one or more of the following features. For example, the alkyl group of compound of Formula IV may be 1 to 6 carbon atoms. The Compound of Formula IV may be triethyl orthoformate.

The trifluoroacetic acid may be added drop-wise at a temperature of about 20° C. to about reflux and Step b) may further include refluxing for a period of about 1 hour to about 48 hours.

Isolation of the erlotinib trifluoroacetate may be carried out by filtration, solvent removal, layer separation, centrifugation, concentration, distillation, or a combination thereof.

Figure 1:
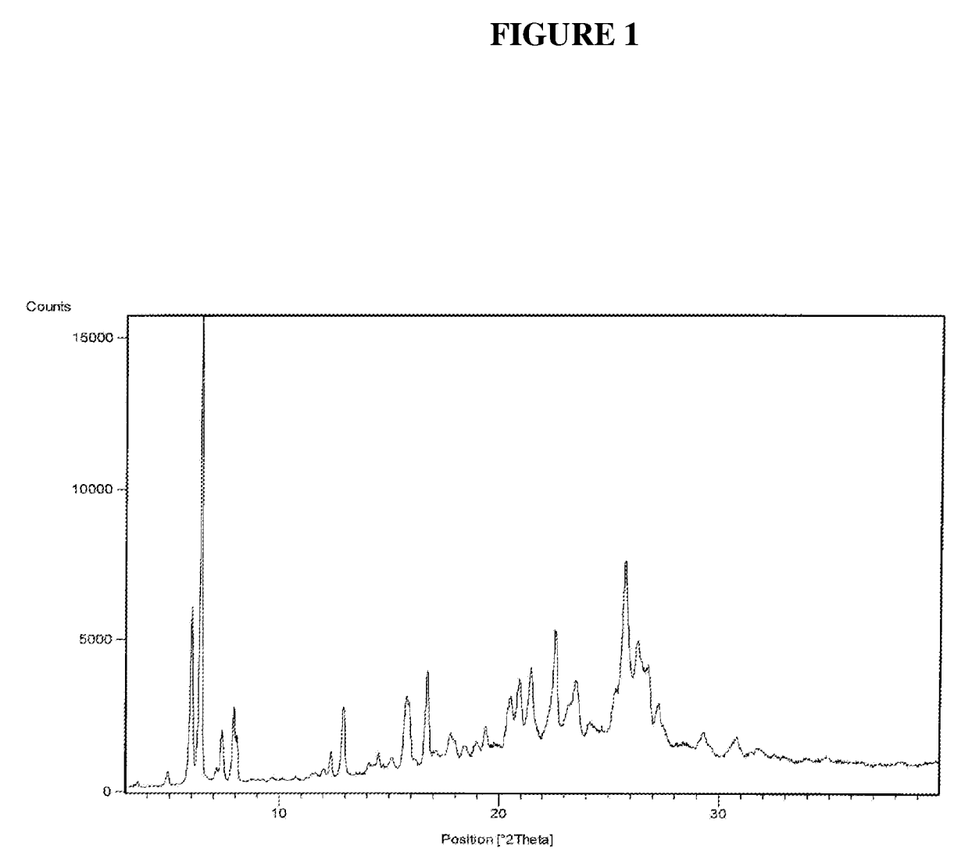

In yet another general aspect there is provided erlotinib trifluoroacetate Form E having typical XRPD pattern as depicted in FIG. 1.

In another general aspect there is provided erlotinib trifluoroacetate Form E characterized by a powder XRD pattern, which includes peaks at about 6.43±0.2θ, 16.73±0.2θ, 22.55±0.2θ, 25.72±0.2θ, and 26.25±0.2θ.

Embodiments of this aspect may include one or more of the following features. For example, the erlotinib trifluoroacetate Form E may further include 2θ values at 6.00±0.2θ, 7.92±0.2θ, 12.94±0.2θ, 15.74±0.2θ, 20.52±0.2θ, 20.90±0.2θ, 21.43±0.2θ, 23.54±0.2θ, 25.25±0.2θ, 26.50±0.2θ, and 26.75±0.2θ.

In another general aspect there is provided a process for the preparation of erlotinib trifluoroacetate Form E. The process includes:
a) treating erlotinib base with trifluoroacetic acid; and
b) isolating erlotinib trifluoroacetate.

Embodiments of this aspect may include one or more of the following features. For example, the erlotinib base may be dissolved or slurried in an organic solvent. In addition, the treatment of erlotinib base with trifluoroacetic acid may be carried out at a temperature of about 20° C. to about reflux.

Isolation of the erlotinib trifluoroacetate may be carried out by filtration, solvent removal, layer separation, centrifugation, concentration, distillation, or a combination thereof.

In yet another general aspect there is provided a process for the preparation of erlotinib trifluoroacetate Form E. The process includes:
a) mixing 2-amino-4,5-bis(2-methoxyethoxy)benzonitrile, 3-ethynyl aniline and compound of Formula IV, wherein R is alkyl group;

HC(OR)₃             Formula IV b) contacting the mixture obtained in step a) with trifluoroacetic acid; and
c) isolating erlotinib trifluoroacetate.

Embodiments of this aspect may include one or more of the following features. For example, the alkyl group of compound of Formula IV comprises 1 to 6 carbon atoms. The compound of Formula IV may be triethyl orthoformate.

The trifluoroacetic acid may be added drop-wise at a temperature of about 20° C. to about reflux. Step b) may further include refluxing for a period of about 1 hour to about 48 hours. Isolation of the erlotinib trifluoroacetate Form E may be carried out by filtration, solvent removal, layer separation, centrifugation, concentration, distillation, or a combination thereof.

In a final general aspect there is provided an improved process for the preparation of erlotinib hydrochloride. The process includes:
a) treating erlotinib trifluoroacetate with hydrochloric acid; and
b) isolating erlotinib hydrochloride.

Embodiments of this aspect may include one or more of the following features. For example, Step a) may further include treating erlotinib trifluoroacetate in a solvent selected from alcohols, water or mixture thereof. The hydrochloric acid may be hydrochloride gas or hydrochloric acid solution.

Step a) may be carried out at a temperature of about 20° C. to about 40° C. and isolation of the erlotinib hydrochloride may be carried out by filtration, solvent removal, layer separation, centrifugation, concentration, distillation, or a combination thereof.

DETAILED DESCRIPTION OF THE INVENTION

One aspect of the present invention provides a process for preparing erlotinib or its pharmaceutically acceptable salt thereof which comprises treating 2-amino-4,5-bis (2-methoxyethoxy)benzonitrile of Formula II, Formula II with 3-ethynyl aniline of Formula III Formula III and a Compound of Formula IV HC(OR)₃             Formula IV wherein R is alkyl group.

The term "alkyl", as used herein, unless otherwise indicated, means an aliphatic hydrocarbon group which may be straight or branched and comprising about 1 to about 6 carbon atoms in the chain. Branched means that one or more lower alkyl groups, such as, methyl, ethyl or propyl, are attached to a linear alkyl chain.

The 2-amino-4,5-bis(2-methoxyethoxy)benzonitrile may be obtained by any of the methods known in the art including those described in WO 2007/138612.

The 2-amino-4,5-bis(2-methoxyethoxy)benzonitrile may be taken as a solution.

The solution of 2-amino-4,5-bis(2-methoxyethoxy)benzonitrile may be obtained by dissolving 2-amino-4,5-bis(2-methoxyethoxy)benzonitrile in an organic solvent.

There are no specific limitations with respect to the organic solvent employed in the reaction, so far as the solvent does not participate in the reaction. The solvent used for the dissolution of 2-amino-4,5-bis(2-methoxyethoxy)benzonitrile include alcohols, such as, methanol, ethanol, n-propanol, 2-propanol, n-butanol, 2-butanol; aromatic hydrocarbon, such as, benzene, toluene, and xylene, substituted toluenes, substituted xylenes; halogenated hydrocarbons, such as, dichloromethane, dichloroethane, trichloroethane, tetrachloroethane, dichloropropane, chloroform, carbon tetrachloride; ethers, such as, diethyl ether, diisopropyl ether, tert-butyl methyl ether, dioxane, tetrahydrofuran; ketones, such as, acetone, methyl ethyl ketone, methyl isobutyl ketone; alkyl acetate, such as, ethyl acetate, n-propyl acetate, isopropyl acetate, n-butyl acetate, isobutyl acetate; alkyl nitriles, such as, acetonitrile, propionitrile; amides, such as, N,N-dimethylformamide; dimethyl sulfoxide. Preferred are alcohols. More preferred is 2-propanol. The organic solvents may be employed singly or in combination.

The amount of organic solvent employed in the reaction depends on the homogeneity and stirring conditions of the reaction mixture.

The solution of 2-amino-4,5-bis(2-methoxyethoxy)benzonitrile may be added to a solution of 3-ethynyl aniline and a compound of Formula IV, Formula IV wherein R is alkyl group.

The solution of 3-ethynyl aniline and a compound of Formula IV,

Formula IV wherein R is alkyl group may further contain an acid catalyst, such as, acetic acid, trifluoroacetic acid, formic acid.

The mixture may also be obtained by adding 2-amino-4,5-bis(2-methoxyethoxy)benzonitrile; 3-ethynyl aniline; a compound of Formula IV and an acid catalyst in optional order of succession.

The mixture obtained may be stirred and after stirring may be heated to reflux at a temperature in the range of 30° C. to 135° C. for about 3 hours to about 24 hours. The reaction mass may be cooled to room temperature and the pH may be adjusted to about 3.0 to about 4.0 with a suitable acid in a suitable solvent.

Pharmaceutically acceptable salts of erlotinib may be prepared by treating erlotinib base with a corresponding acid in a suitable solvent. Suitable pharmaceutically acceptable salts of erlotinib include salts of erlotinib base with acetic acid, benzoic acid, fumaric acid, benzoic acid, maleic acid, citric acid, tartaric acid, methanesulfonic acid, ethanesulfonic acid, benzenesulfonic acid, p-toluene sulfonic acid, hydrochloric acid, hydrobromic acid and sulfuric acid.

Suitable solvent include alcohols, such as, methanol, ethanol, n-propanol, 2-propanol, n-butanol, 2-butanol; aromatic hydrocarbon, such, as benzene, toluene, and xylene, substituted toluenes, substituted xylenes; halogenated hydrocarbons, such as, dichloromethane, dichloroethane, trichloroethane, tetrachloroethane, dichloropropane, chloroform, carbon tetrachloride; ethers, such as, diethyl ether, diisopropyl ether, tert-butyl methyl ether, dioxane, tetrahydrofuran; ketones, such as, acetone, methyl ethyl ketone, methyl isobutyl ketone; alkyl acetate, such as, ethyl acetate, n-propyl acetate, isopropyl acetate, n-butyl acetate, isobutyl acetate; alkyl nitriles, such as, acetonitrile, propionitrile; amides, such as, N,N-dimethylformamide; dimethyl sulfoxide. Preferred are alcohols. More preferred is 2-propanol. The organic solvents may be employed singly or in combination.

Another aspect of the present invention provides a process for the preparation of erlotinib trifluoroacetate which comprises:
a) treating erlotinib base with trifluoroacetic acid; and
b) isolating erlotinib trifluoroacetate.

Erlotinib base prepared by any method known in the art can be used as starting material. Step a) includes dissolving or slurring erlotinib in an organic solvent or obtaining an existing solution from a previous processing step of erlotinib in an organic solvent.

Trifluoro acetic acid may be added to erlotinib free base step-wise in about 2-3 equal portions. Trifluoro acetic acid may be also added drop-wise at a temperature of about 20° C. to about reflux, preferably at about 25° C. to about 30° C., followed by stirring the reaction mass for about 10 minutes to about 90 minutes preferably for about 20 minutes to about 30 minutes, at a temperature of about 20° C. to about 40° C., preferably at about 25° C. to about 30° C. The mixture obtained is refluxed for a period of about 1 hour to about 48 hours preferably for a period of 24 hours.

Step b) of isolating erlotinib trifluoroacetate may be carried out by any method known in the art, such as, filtration, solvent removal, layer separation, centrifugation, concentration, distillation, or a combination thereof.

Preferably, the obtained erlotinib trifluoroacetate salt is further dried at an elevated temperature, preferably, under reduced pressure (less than 1 atmosphere, more preferably, about 10 mbar to about 100 mbar, and, most preferably, about 10 mbar to about 25 mbar). Preferably, the drying is carried out at a temperature between about 35° C. and about 60° C., more preferably, between about 40° C. and about 45° C. Preferably the drying takes place over a period of about 8 hours to about 36 hours, more preferably, about 10 hours to about 24 hours, and most preferably, about 18 hours.

Another aspect of the present invention provides a process for the preparation of erlotinib trifluoroacetate which comprises:
a) providing a mixture of 2-amino-4,5-bis(2-methoxyethoxy)benzonitrile, 3-ethynyl aniline and a compound of Formula IV, wherein R is alkyl group;

Formula IV b) contacting the mixture obtained in step a) with trifluoroacetic acid; and
c) isolating erlotinib trifluoroacetate.

The term "alkyl", as used herein, unless otherwise indicated, means an aliphatic hydrocarbon group which may be straight or branched and comprising about 1 to about 6 carbon atoms in the chain. Branched means that one or more lower alkyl groups, such as, methyl, ethyl or propyl, are attached to a linear alkyl chain.

The 2-amino-4,5-bis(2-methoxyethoxy)benzonitrile may be obtained by any of the methods known in the art including those described in WO 2007/138612.

Step a) of providing a mixture of 2-amino-4,5-bis(2-methoxyethoxy)benzonitrile, 3-ethynyl aniline and compound of Formula IV, includes dissolving 2-amino-4,5-bis (2-methoxyethoxy)benzonitrile in an organic solvent to form a solution and then adding 3-ethynyl aniline and a compound of Formula IV to the obtained solution.

3-ethynyl aniline and a compound of Formula IV may be added to the solution of 2-amino-4,5-bis(2-methoxyethoxy)benzonitrile in an organic solvent at a temperature of about 20° C. to about 75° C., preferably at about 20° C. to about 60° C., more preferably at about 20° C. to about 40° C.

The mixture of step a) may also be obtained by adding 2-amino-4,5-bis (2-methoxyethoxy)benzonitrile; 3-ethynyl aniline; a Compound of Formula IV in a suitable solvent in any order of succession.

There are no specific limitations with respect to the organic solvent employed, so far as the solvent does not participate in the reaction.

Suitable solvents used for the dissolution of 2-amino-4,5-bis(2-methoxyethoxy)benzonitrile include alcohols, such as, methanol, ethanol, n-propanol, 2-propanol, n-butanol, 2-butanol; aromatic hydrocarbon, such as, benzene, toluene, and xylene, substituted toluenes, substituted xylenes; halogenated hydrocarbons, such as, dichloromethane, dichloroethane, trichloroethane, tetrachloroethane, dichloropropane, chloroform, carbon tetrachloride; ethers, such as, diethyl ether, diisopropyl ether, tert-butyl methyl ether, dioxane, tetrahydrofuran; ketones, such as, acetone, methyl ethyl ketone, methyl isobutyl ketone; alkyl acetate, such as, ethyl acetate, n-propyl acetate, isopropyl acetate, n-butyl acetate, isobutyl acetate; alkyl nitriles, such as, acetonitrile, propionitrile; amides, such as, N,N-dimethylformamide; dimethyl sulfoxide. Preferred are alcohols. More preferred is methanol, ethanol or 2-propanol. The organic solvents may be employed singly or in combination.

Step b) involves contacting the mixture obtained in step a) with trifluoroacetic acid. Trifluoro acetic acid may be added step-wise in about 2 to 3 equal portions to the mixture obtained in step a).

Trifluoro acetic acid may be also added drop-wise at a temperature of about 20° C. to about reflux, preferably at about 25° C. to about 30° C., followed by stirring the reaction mass for about 10 minutes to about 90 minutes preferably for about 20 minutes to about 30 minutes at a temperature of about 20° C. to about 40° C., preferably at about 25° C. to about 30° C.

The mixture obtained in step b) is refluxed for a period of about 1 hour to about 48 hours preferably for a period of 24 hours.

Step c) of isolating erlotinib trifluoroacetate may be carried out by any method known in the art, such as, filtration, solvent removal, layer separation, centrifugation, concentration, distillation, or a combination thereof.

Preferably, the obtained erlotinib trifluoroacetate salt is further dried at an elevated temperature, preferably, under reduced pressure (less than 1 atmosphere, more preferably, about 10 mbar to about 100 mbar, and, most preferably, about 10 mbar to about 25 mbar). Preferably, the drying is carried out at a temperature between about 35° C. and about 60° C., more preferably, between about 40° C. and about 45° C. Preferably the drying takes place over a period of about 8 hours to about 36 hours, more preferably, about 10 hours to about 24 hours, and, most preferably, about 18 hours.

Figure 2:
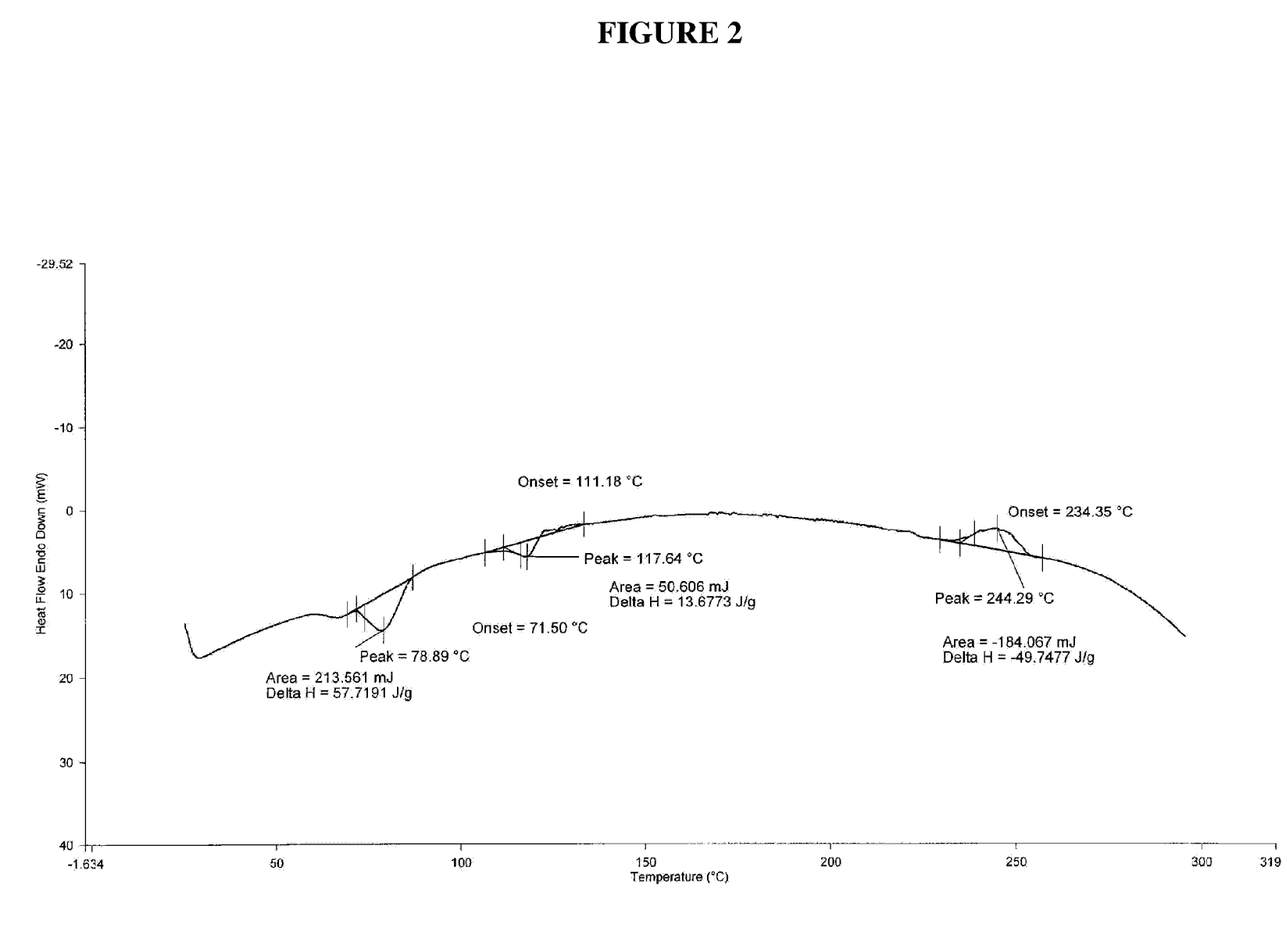
FIG. 2 depicts DSC of Form E of erlotinib trifluoroacetate.
Figure 3:
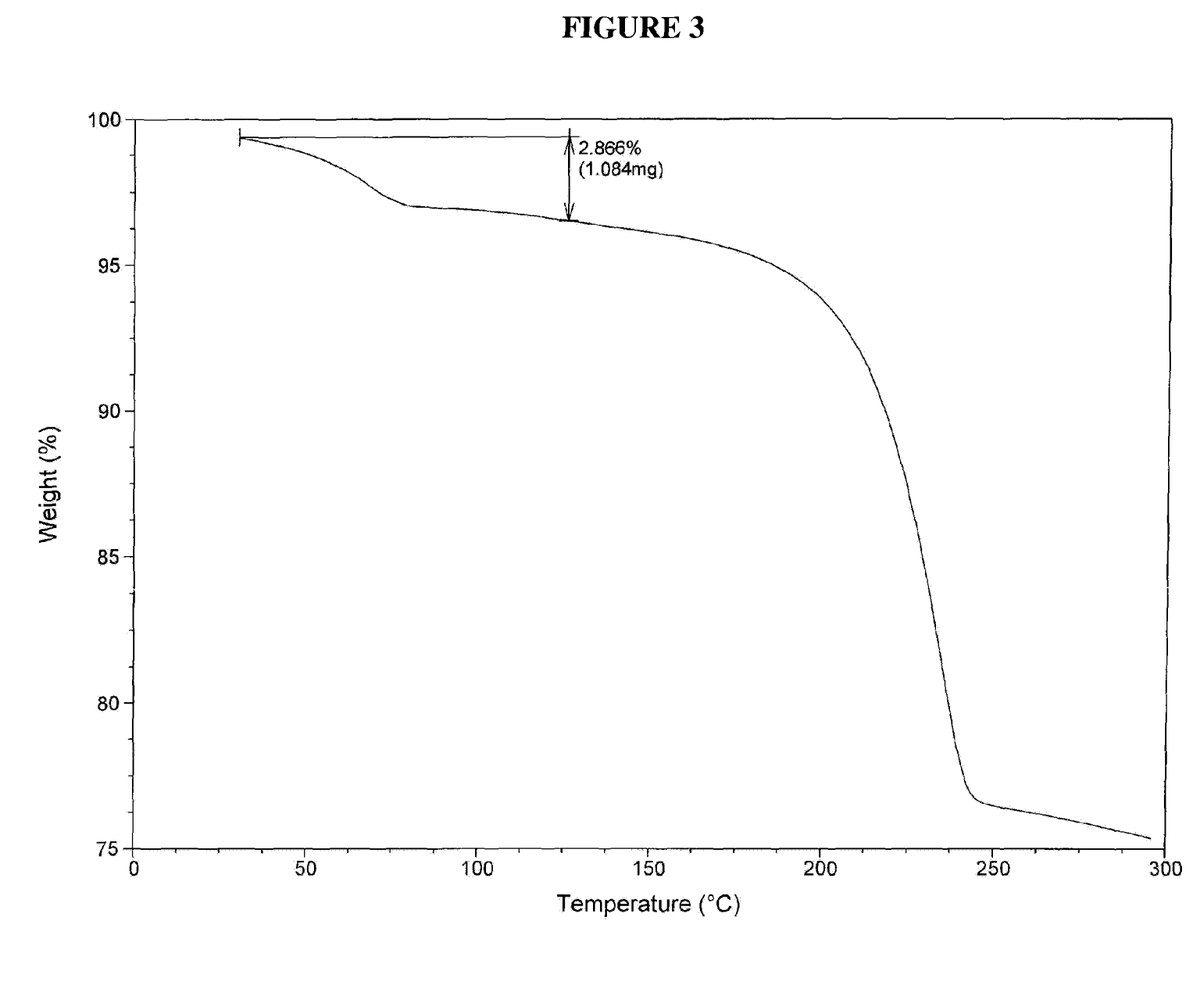
FIG. 3 depicts TGA of Form E of erlotinib trifluoroacetate.

Yet another aspect of the present invention provides a novel polymorphic Form E of erlotinib trifluoroacetate having typical XRPD pattern as depicted in FIG. 1 of the accompanied drawing. The XRPD of Form E of erlotinib trifluoroacetate exhibits characteristic 2θ values at 6.43±0.2 θ, 16.73±0.2θ, 22.55±0.2θ, 25.72±0.2θ, 26.25±0.2 Form E of erlotinib trifluoroacetate may be further characterized by XRPD pattern comprising 2θ values at 6.00±0.2θ, 7.92±0.2θ, 12.94±0.2θ, 15.74±0.2θ, 20.52±0.2θ, 20.90±0.2θ, 21.43±0.2θ, 23.54±0.2θ, 25.25±0.2θ, 26.50±0.2θ, 26.75±0.2θ. The novel polymorphic Form E of erlotinib trifluoroacetate has the X-ray diffractogram which shows characteristic peaks expressed as interplanar distance at approximately 13.72, 5.29, 3.94, 3.46, 3.39 Å. Form E of erlotinib trifluoroacetate may be further characterized by peaks expressed as interplanar distance at approximately 14.71, 11.15, 6.84, 5.62, 4.32, 4.24, 4.14, 3.77, 3.52, 3.36, 3.33 Å. The novel polymorphic Form E of erlotinib trifluoroacetate has characteristic DSC thermogram as depicted in FIG. 2 of the accompanied drawing. The DSC thermogram shows a characteristic peaks at about 79° C., at about 118° C., and at about 244° C.

Another aspect, the invention provides a process for the preparation of Form E of erlotinib trifluoroacetate which comprises:
a) treating erlotinib base with trifluoroacetic acid; and
b) isolating Form E of erlotinib trifluoroacetate.

Erlotinib base prepared by any method known in the art can be used as starting material. Step a) includes dissolving or slurring erlotinib in an organic solvent or obtaining an existing solution from a previous processing step of erlotinib in an organic solvent.

Trifluoro acetic acid may be added to erlotinib free base step-wise in about 2 to 3 equal portions. Trifluoro acetic acid may be also added drop-wise at a temperature of about 20° C. to about reflux, preferably at about 25° C. to about 30° C., followed by stirring the reaction mass for about 10 minutes to about 90 minutes preferably for about 20 minutes to about 30 minutes at a temperature of about 20° C. to about 40° C., preferably at about 25° C. to about 30° C.

The mixture obtained is refluxed for a period of about 1 hour to about 48 hours preferably for a period of 24 hours.

Step b) of isolating erlotinib trifluoroacetate may be carried out by any method known in the art, such as, filtration, solvent removal, layer separation, centrifugation, concentration, distillation, or a combination thereof.

Preferably, the obtained erlotinib trifluoroacetate salt is further dried at elevated temperature, preferably, under reduced pressure (less than 1 atmosphere, more preferably, about 10 mbar to about 100 mbar, and, most preferably, about 10 mbar to about 25 mbar). Preferably, the drying is carried out at a temperature between about 35° C. and about 60° C., more preferably, between about 40° C. and about 45° C. Preferably the drying takes place over a period of about 8 hours to about 36 hours, more preferably, about 10 hours to about 24 hours, and, most preferably, about 18 hours.

Another aspect, the invention provides a process for the preparation of Form E of erlotinib trifluoroacetate which comprises:
a) providing a mixture of 2-amino-4,5-bis(2-methoxyethoxy)benzonitrile, 3-ethynyl aniline and compound of Formula IV, wherein R is alkyl group;

HC(OR)₃          Formula IV b) contacting the mixture obtained in step a) with trifluoroacetic acid; and
c) isolating Form E of erlotinib trifluoroacetate.

The term "alkyl" as used herein, unless otherwise indicated, means an aliphatic hydrocarbon group which may be straight or branched and comprising about 1 to about 6 carbon atoms in the chain. Branched means that one or more lower alkyl groups, such as, methyl, ethyl or propyl, are attached to a linear alkyl chain.

2-amino-4,5-bis(2-methoxyethoxy)benzonitrile may be obtained by any of the methods known in the art including those described in WO 2007/138612.

Step a) of providing a mixture of 2-amino-4,5-bis(2-methoxyethoxy)benzonitrile, 3-ethynyl aniline and compound of Formula IV, includes dissolving 2-amino-4,5-bis(2-methoxyethoxy)benzonitrile in an organic solvent to form a solution and then adding 3-ethynyl aniline and a compound of Formula IV to the obtained solution.

3-ethynyl aniline and a compound of Formula IV may be added to the solution of 2-amino-4,5-bis(2-methoxyethoxy) benzonitrile in an organic solvent at a temperature of about 20° C. to about 75° C., preferably at about 20° C. to about 60° C., more preferably at about 20° C. to about 40° C.

The mixture of step a) may also be obtained by adding 2-amino-4,5-bis(2-methoxyethoxy)benzonitrile; 3-ethynyl aniline; a compound of Formula IV in a suitable solvent in any order of succession.

There are no specific limitations with respect to the organic solvent employed, so far as the solvent does not participate in the reaction.

Suitable solvent used for the dissolution of 2-amino-4,5-bis(2-methoxyethoxy)benzonitrile include alcohols, such as, methanol, ethanol, n-propanol, 2-propanol, n-butanol, 2-butanol; aromatic hydrocarbon, such as, benzene, toluene, and xylene, substituted toluenes, substituted xylenes; halogenated hydrocarbons, such as, dichloromethane, dichloroethane, trichloroethane, tetrachloroethane, dichloropropane, chloroform, carbon tetrachloride; ethers, such as, diethyl ether, diisopropyl ether, tert-butyl methyl ether, dioxane, tetrahydrofuran; ketones, such as, acetone, methyl ethyl ketone, methyl isobutyl ketone; alkyl acetate, such as, ethyl acetate, n-propyl acetate, isopropyl acetate, n-butyl acetate, isobutyl acetate; alkyl nitriles, such as, acetonitrile, propionitrile;

amides, such as, N,N-dimethylformamide; dimethyl sulfoxide. Preferred are alcohols. More preferred is methanol, ethanol or 2-propanol. The organic solvents may be employed singly or in combination.

Step b) involves contacting the mixture obtained in step a) with trifluoroacetic acid. Trifluoro acetic acid may be added step-wise in about 2 to 3 equal portions to the mixture obtained in step a). Trifluoro acetic acid may be also added drop-wise at a temperature of about 20° C. to about reflux, preferably at about 25° C. to about 30° C., followed by stirring the reaction mass for about 10 minutes to about 90 minutes preferably for about 20 minutes to about 30 minutes at a temperature of about 20° C. to about 40° C., preferably at about 25° C. to about 30° C.

The mixture obtained in step b) is refluxed for a period of about 1 hour to about 48 hours preferably for a period of 24 hours.

Step c) of isolating form E of erlotinib trifluoroacetate may be carried out by any method known in the art, such as, filtration, solvent removal, layer separation, centrifugation, concentration, distillation, or a combination thereof.

Preferably, the obtained erlotinib trifluoroacetate salt is further dried at an elevated temperature, preferably, under reduced pressure (less than 1 atmosphere, more preferably, about 10 mbar to about 100 mbar, and, most preferably, about 10 mbar to about 25 mbar). Preferably, the drying is carried out at a temperature between about 35° C. and about 60° C., more preferably, between about 40° C. and about 45° C. Preferably the drying takes place over a period of about 8 hours to about 36 hours, more preferably, about 10 hours to about 24 hours, and, most preferably, about 18 hours.

Yet another aspect of the present invention provides a process for the preparation of erlotinib hydrochloride which comprises:
 a) treating erlotinib trifluoroacetate with hydrochloric acid; and
 b) isolating erlotinib hydrochloride.

Step a) of treating erlotinib trifluoroacetate with hydrochloric acid includes treating erlotinib trifluoroacetate in a solvent selected from alcohols, water or mixture thereof, preferably methanol, ethanol, isopropanol, n-butanol, isobutanol, tert-butanol, water or mixtures thereof, more preferably isopropyl alcohol, water or mixture thereof at a temperature of about 20° C. to about 50° C. preferably at a temperature of about 25° C. to about 30° C. and treating the mixture with hydrochloric acid where in hydrochloric acid can be hydrochloride gas or hydrochloric acid solution at a temperature of about 20° C. to about 40° C., preferably at a temperature of about 25° C. to about 30° C.

Step b) of isolating erlotinib hydrochloride may be carried out by any method known in the art, such as, filtration, solvent removal, layer separation, centrifugation, concentration, distillation, or a combination thereof.

DRAWINGS OF THE INVENTION

FIG. 1 and FIG. 1*a* depicts XRPD of Form E of crystalline erlotinib trifluoroacetate and the associated values, respectively.

Powder XRD of the samples were determined by using X-Ray Difractometer, PANalytical X' pert PRO.

DSC thermograms were recorded using Perkin Elmer Diamond DSC, Sample weight: 3 mg to 7 mg, Temperature range: 50° C. to 300° C., Heating rate: 10° C./min, Nitrogen 50.0 mL/min, Number of holes in the crucible: 1.

TGA thermograms were recorded using QA500, Waters TGA instrument, Sample weight: 10 mg to 50 mg, Temperature range: 0 to 300° C.

While the present invention has been described in terms of its specific embodiments, certain modifications and equivalents will be apparent to those skilled in the art and are intended to be included within the scope of the present invention.

EXAMPLES

Example 1

Preparation of Erlotinib Hydrochloride

To a solution of 2-amino-4,5-bis(2-methoxyethoxy)benzonitrile (5.0 g) in isopropanol (25.0 ml) was added drop-wise a solution of triethyl orthoformate (4.0 g); 3-ethnylphenylamine (3.45 g) and acetic acid (0.2 ml). The mixture was stirred and heated at reflux for 4 hours. The reaction progress was monitored by TLC. After completion of the reaction, the reaction mass was cooled to room temperature and the pH was adjusted to 3.0 to 4.0 with isopropanolic hydrochloride (3.0 ml). The reaction mixture was stirred for 2 hours at room temperature. The solid was filtered, washed with isopropyl alcohol and dried on the air oven to obtain the titleCompound.
Yield: 3.0 g

Example 2

Preparation of Erlotinib Hydrochloride

A solution of 2-amino-4,5-bis(2-methoxyethoxy)benzonitrile (1.0 g) in isopropanol (20 ml) was added dropwise to a solution of triethyl orthoformate (0.8 g); 3-ethnylphenylamine (0.69 g) and acetic acid (0.2 ml). This mixture was stirred and heated at reflux for 4 hours. The reaction progress was monitored by TLC. After completion of the reaction, the reaction mass was cooled to room temperature and the pH was adjusted to 3.0 to 4.0 with methanolic hydrochloride (1.0 ml). The reaction mixture was stirred for 2 hours at room temperature. The solid was filtered, washed with isopropyl alcohol and dried on the air oven to obtain the title compound.
Yield: 0.5 g

Example 3

Preparation of Erlotinib Trifluoroacetate

2-Amino-4,5-bis(2-methoxyethoxy)benzonitrile (25 g) was charged into ethanol (350 ml) at 25° C. to 30° C. and stirred for 10 minutes to 15 minutes to get a clear solution. 3-ethynyl aniline (11.1 g) followed triethyl orthoformate (20.86 g) was charged into reaction mass at 25° C. to 30° C. Trifluoroacetic acid (3.8 ml) was added slowly drop-wise into the reaction mixture at 25° C. to 30° C. and stirred for 30 minutes at 25° C. to 30° C. Trifluoroacetic acid (3.8 ml) was added slowly drop wise to reaction mixture at 25° C. to 30° C. and stirred for 30 minutes at 25° C. to 30° C. Again, trifluoroacetic acid (3.8 ml) was added slowly drop wise to reaction mixture at 25° C. to 30° C. and stirred for 30 minutes at 25° C. to 30° C. The reaction mixture was refluxed for about 24 hours at 75° C. to 80° C. and Cooled to 25° C. to 30° C. Ethanol (~150 ml) was recovered from the reaction mixture under vacuum at 55° C. to 60° C. The solution obtained was Cooled to 25° C. to 30° C. and stirred for about 18 hours at 25° C. to 30° C. The solid obtained was filtered, washed with ethanol (2×25 ml) and dried under vacuum for about 18 hours at 40° C. to 45° C. to give erlotinib trifluoroacetate.

Yield: 29.2 g
Purity: 97.35%

Example 4

Preparation of Erlotinib Hydrochloride from Erlotinib Trifluoroacetate

Erlotinib trifluoroacetate salt (10 g) was charged into deionized water (DI water) (80 ml) at 25° C. to 30° C. 35% Concentrated hydrochloric acid (aqueous, 12 ml) was added slowly to reaction mixture at 25° C. to 30° C. and stirred for about 2 hours at 25° C. to 30° C. The solid obtained was filtered, washed with DI water (2×15 ml) and dried under vacuum for about 18 hours at 40° C. to 45° C. to give erlotinib hydrochloride.

Yield: 5.13 g

Example 5

Preparation of Erlotinib Hydrochloride from Erlotinib Trifluoroacetate Erlotinib trifluoroacetate salt (10 g) was charged in to isopropyl alcohol (60 ml) at 25° C. to 30° C. 7.5% isopropanolic hydrochloride (13 ml) was added slowly to the reaction mixture at 25° C. to 30° C. and stirred for about 2 hours at 25° C. to 30° C. The solid obtained was filtered, washed with DI water (2×15 ml), suck dried and dried under vacuum for about 18 hours at 40° C. to 45° C. to give erlotinib hydrochloride.

Yield: 8.08 g

The invention claimed is:

1. A process for preparing erlotinib of Formula I or its pharmaceutically acceptable salts thereof,

Formula I the process comprising treating 2-amino-4,5-bis(2- methoxyethoxy)benzonitrile of Formula I, Formula II with 3-ethynyl aniline of Formula III Formula III and a Compound of Formula IV HC(OR)$_3$    Formula IV wherein R is alkyl group.

2. A process according to claim 1, further comprising the addition of an acid catalyst selected from the group comprising of acetic acid, trifluoroacetic acid, formic acid.

3. A process according to claim 1, wherein the process further comprises heating the mixture obtained to reflux at a temperature in the range of 30° C. to 135° C.

4. A process according to claim 1, where in the alkyl group of compound of Formula IV comprises 1 to 6 carbon atoms.

5. A process according to claim 4, wherein the compound of Formula IV is triethyl orthoformate.

6. A process according to claim 1, wherein the pharmaceutically acceptable salts of erlotinib is prepared by treating erlotinib with an acid in a suitable solvent.

7. A process for the preparation of erlotinib trifluoroacetate, the process comprising:
 a) mixing 2-amino-4,5-bis(2-methoxyethoxy)benzonitrile, 3-ethynyl aniline and a Compound of Formula IV, wherein R is alkyl group;

HC(OR)$_3$    Formula IV b) contacting the mixture obtained in step a) with trifluoroacetic acid; and
 c) isolating erlotinib trifluoroacetate.

8. A process according to claim 7, wherein the alkyl group of compound of Formula IV comprises 1 to 6 carbon atoms.

9. A process according to claim 7, wherein the trifluoroacetic acid is added drop-wise at a temperature of about 20° C. to about reflux.

10. A process according to claim 7, wherein Step b) further comprises refluxing for a period of about 1 hour to about 48 hours.

\* \* \* \* \*

UNITED STATES PATENT AND TRADEMARK OFFICE
CERTIFICATE OF CORRECTION

PATENT NO. : 8,440,823 B2  Page 1 of 1
APPLICATION NO. : 13/258961
DATED : May 14, 2013
INVENTOR(S) : Balaguru Murugesan et al.

It is certified that error appears in the above-identified patent and that said Letters Patent is hereby corrected as shown below:

In the Specification

Column 9, line 36:

"20 values" should read as -- 2θ values --

Signed and Sealed this
Thirty-first Day of December, 2013

Margaret A. Focarino
*Commissioner for Patents of the United States Patent and Trademark Office*